United States Patent [19]

Hogan

[11] 4,156,815
[45] May 29, 1979

[54] X-RAY CRADLE TOP WITH TILTING MECHANISM

[75] Inventor: William F. Hogan, Woodbury, N.J.

[73] Assignee: Spectrum X-Ray Corporation, Westville, N.J.

[21] Appl. No.: 758,475

[22] Filed: Jan. 11, 1977

[51] Int. Cl.² ............................................. G03B 41/16
[52] U.S. Cl. ................................. 250/439 R; 250/456
[58] Field of Search ............... 250/439, 456, 444, 445, 250/446, 447, 448, 449, 450; 269/322, 323

[56] References Cited

U.S. PATENT DOCUMENTS

| 3,643,604 | 8/1978 | Jones | 269/323 |
| 3,848,132 | 8/1978 | Foderaro | 250/439 |

Primary Examiner—Craig E. Church
Assistant Examiner—T. O'Hare
Attorney, Agent, or Firm—Paul & Paul

[57] ABSTRACT

A cradle top for an X-ray examination table carries a cradle or basket rotatable about its lengthwise axis and is mounted for tilting angulation as well as for movement in the elevational, lengthwise and transverse directions.

4 Claims, 9 Drawing Figures

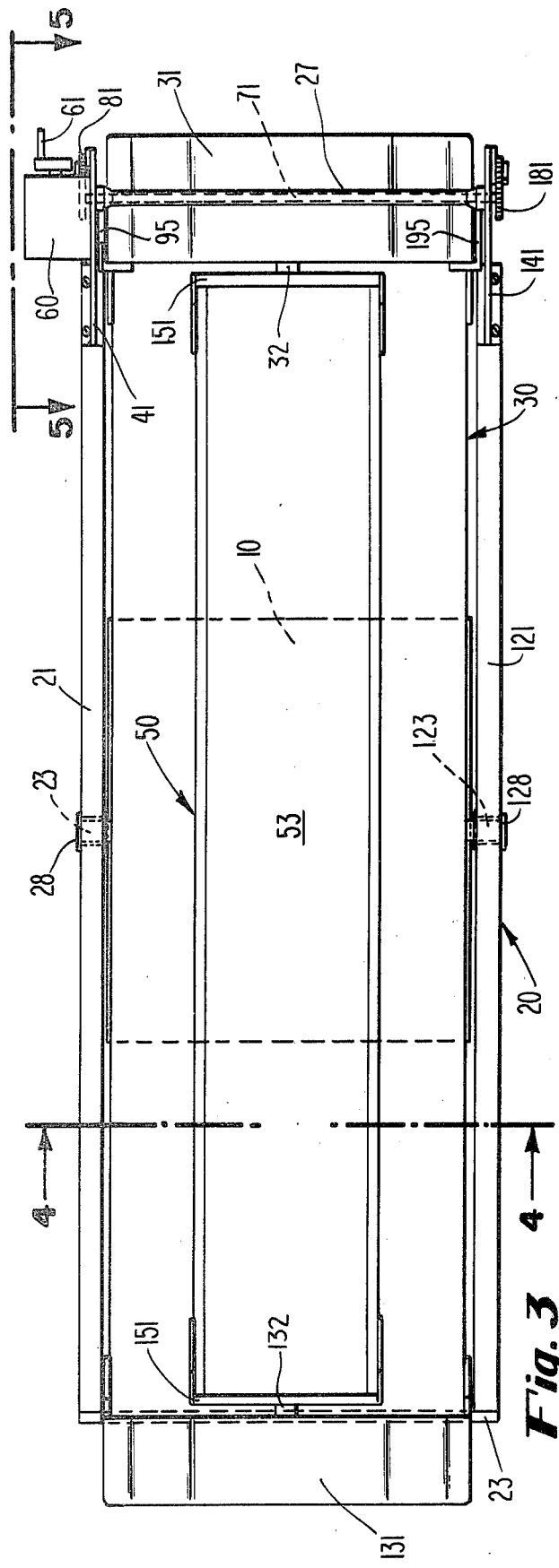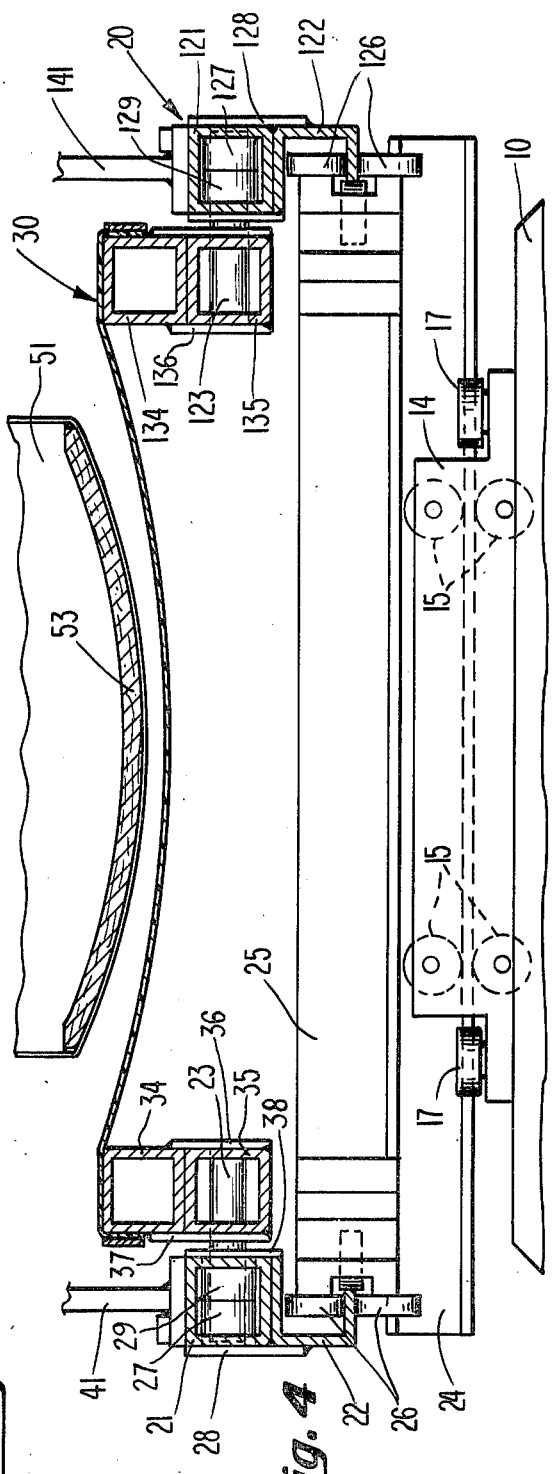
Fig. 3
Fig. 4

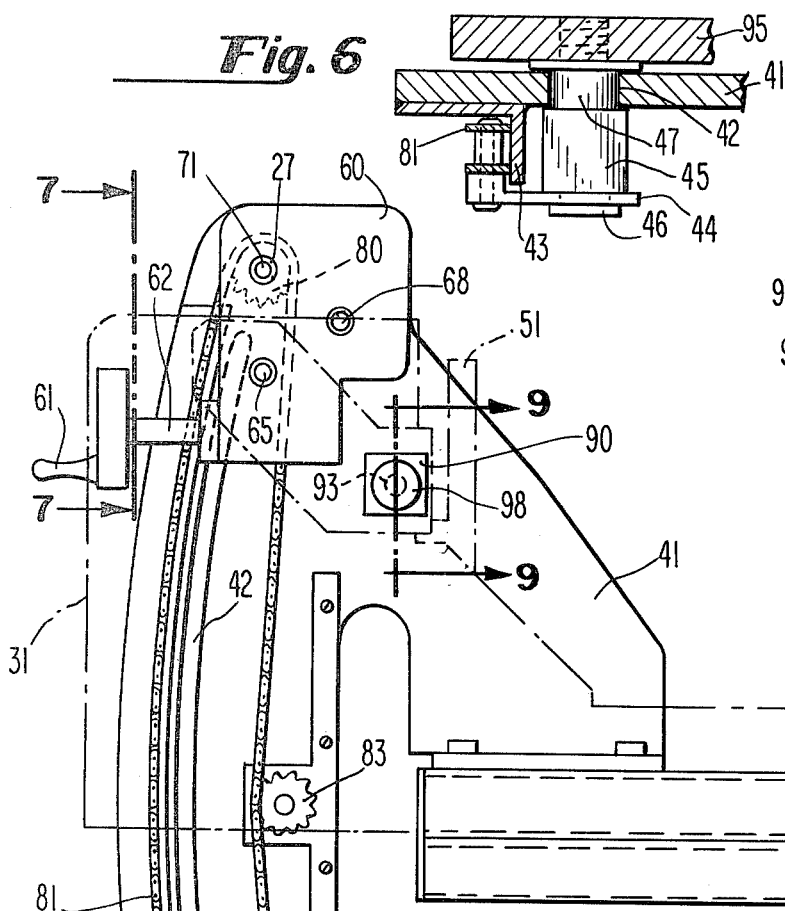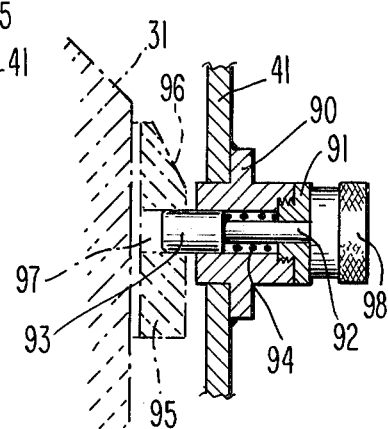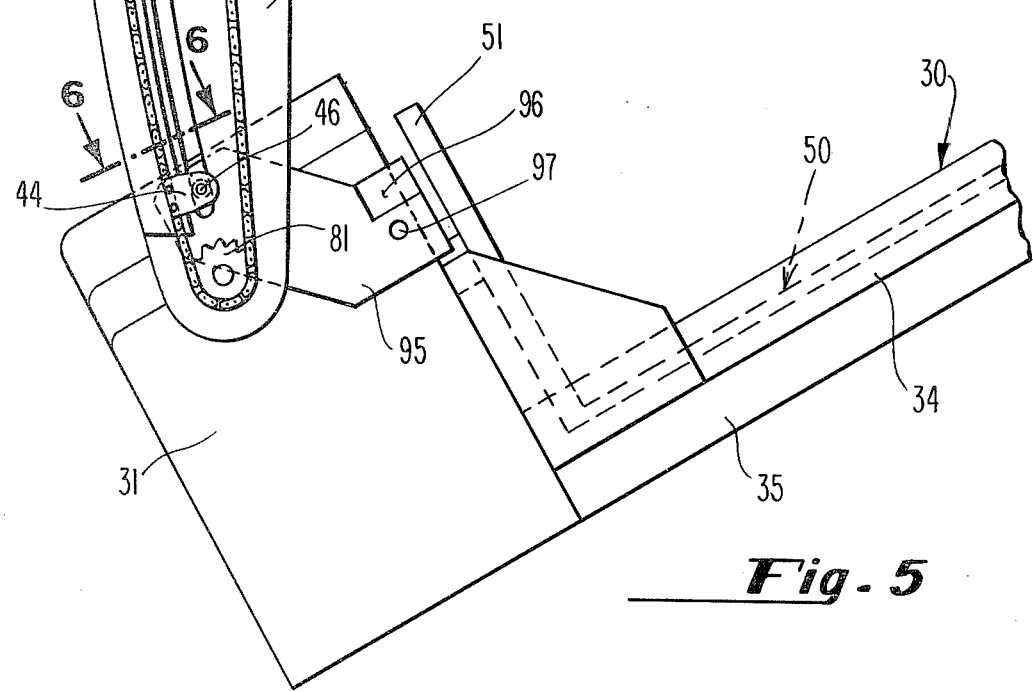

X-RAY CRADLE TOP WITH TILTING MECHANISM

BACKGROUND OF THE INVENTION

This invention relates to X-ray examination work and in particular to cardiology X-ray examination work.

The heart has two valves which occupy positions inclined approximately 30° from the vertical. As a result, X-rays which pass vertically through the patient do not travel through the vessels in these valves, and to obtain the desired X-ray pictures of these heart valves and their vessels, it has been customary, in the prior art, to tilt the X-ray apparatus and the image-receiving apparatus 30° (approximately) from the vertical. By providing a tiltable table top for the patient-receiving rotatable cradle or basket, the need for tilting the X-ray projecting and image-receiving apparatus for cardiology examination is avoided, according to the present invention.

BRIEF DESCRIPTION OF THE DRAWINGS

FIG. 3 is a top plan view of the table top of FIGS. 1 and 2.

FIG. 4 is a view, in section, looking to the right along the line 4—4 of FIG. 3.

FIG. 5 is a side view of the drive chain tilting mechanism looking along the line 5—5 of FIG. 3.

FIG. 6 is a detailed view of the drive chain connector bracket as seen looking along the line 6—6 of FIG. 5.

FIG. 9 is a detailed view of the table-top locking means looking along the line 9—9 of FIG. 5.

SUMMARY OF THE INVENTION

A principal purpose of the present invention is to provide an X-ray examination table for cardiology X-ray examination work which avoids the need for tilting the X-ray projecting and image-receiving apparatus away from the vertical in order to obtain desired X-ray pictures of heart valves and their vessels. The foregoing object is accomplished, in accordance with the present invention, by providing an axially rotatable patient-receiving basket or cradle which is so mounted on a cradle top that, in addition to being elevatable and movable translationally in both the lengthwise and lateral directions, is tiltable about its short transverse axis to a position at least 30° from the horizontal. Tilting of the cradle top provides for convenient perpendicular visualization in the oblique half axial position of the left anterior descending coronary artery and its branches, with minimal patient longitudinal centering adjustment necessary during angulation. Angulation of the patient is accomplished safely and quickly with a simple manual crank handle located at the rear or foot end of the table. In using the manual crank handle, the technician is out of the way of the operator and primary radiation. The technician from this location may, at the option of the operator, also control rotation and re-centering of the patient-holding cradle. When the cradle top tilt mechanism is used in conjunction with a desired form of under table X-ray tube motor drive, the X-ray tube is automatically raised and lowered as the cradle is tilted to its angular position and brought back to horizontal, keeping to a minimum the patient focal-spot distance change.

DETAILED DESCRIPTION OF THE PREFERRED EMBODIMENTS

Figure 1:
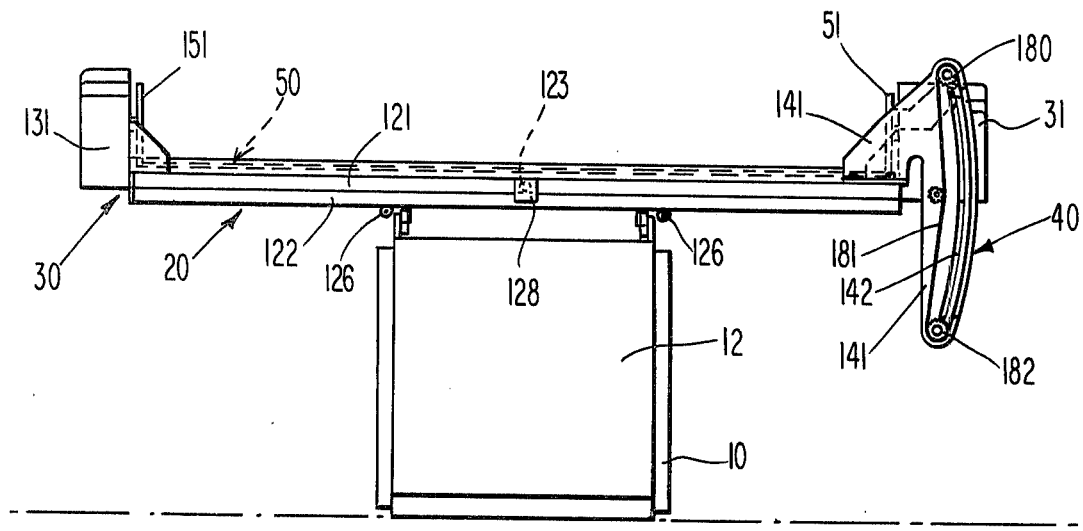
FIG. 1 is a simplified side elevational view of an X-ray examination table provided with a table-top tilting mechanism according to the present invention, but showing the table top in untilted position.
Figure 2:
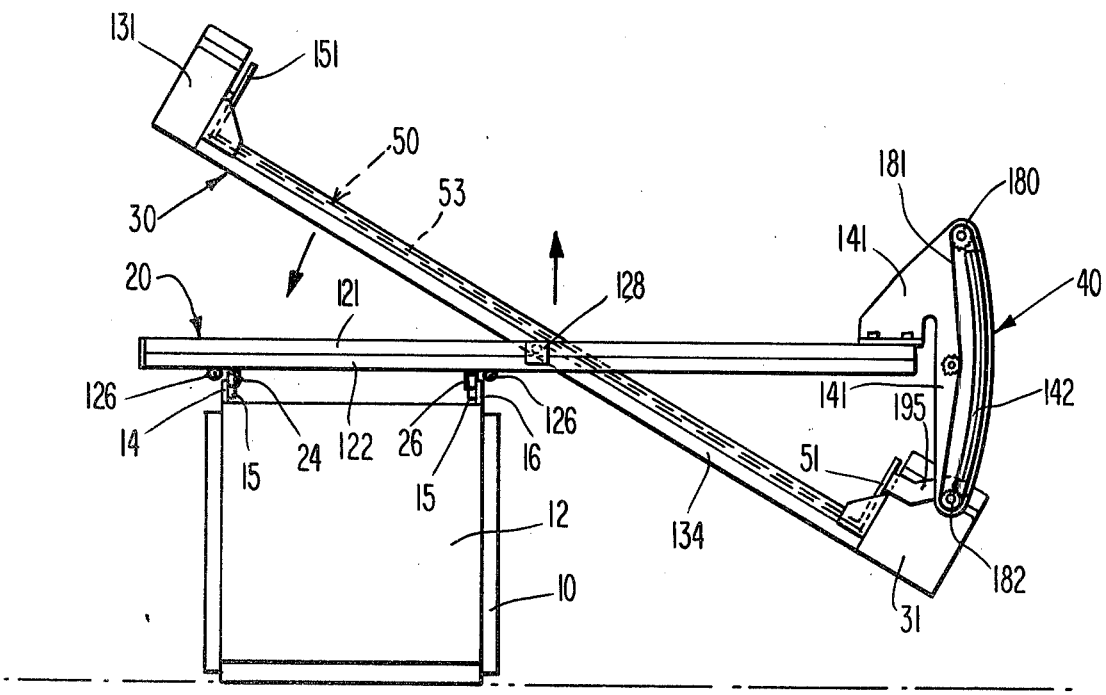
FIG. 2 is a simplified view similar to FIG. 1 showing the table top in tilted position.
Figure 7:
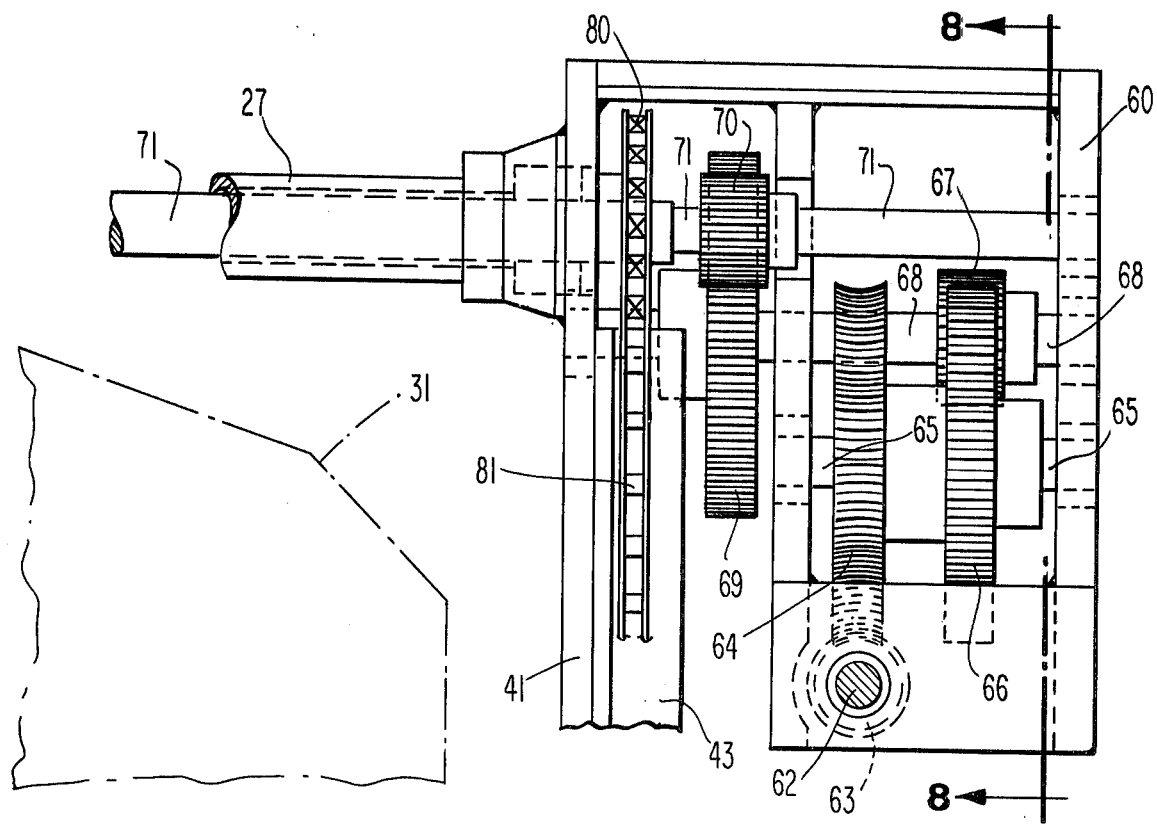
FIG. 7 is a view of the hand-crank shaft and gear reducing means looking along the line 7—7 of FIG. 5.
Figure 8:
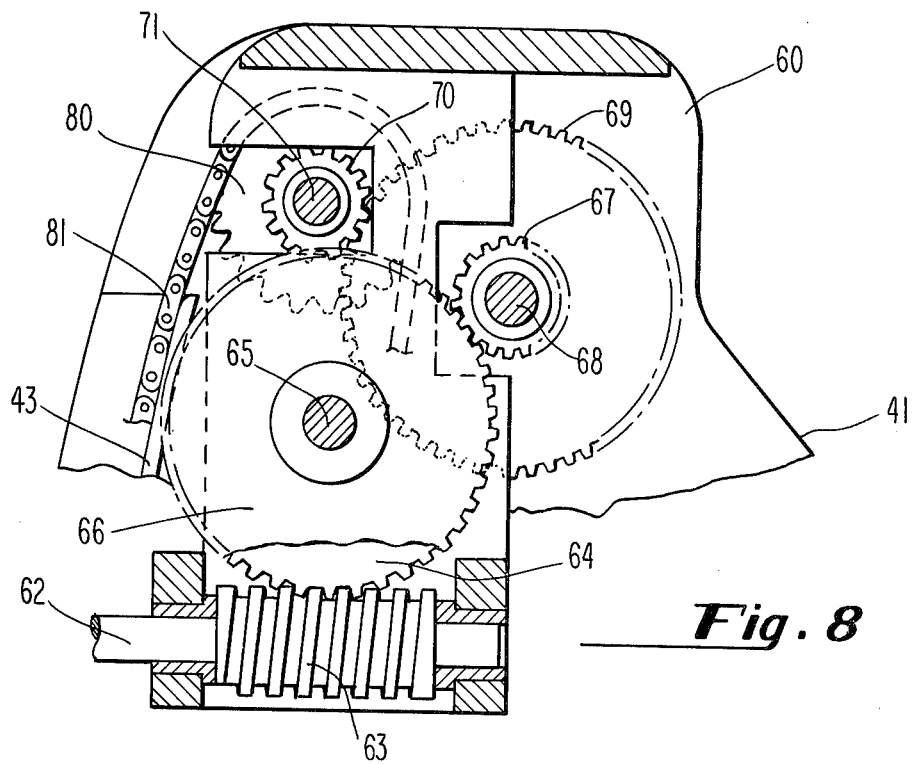
FIG. 8 is a view of the worm drive and gear reducing means looking along the lines 8—8 of FIG. 7.

Referring now to FIGS. 1 and 2, there is shown, in side elevation, simplified illustrations of a tilting table top adapted for cardiology X-ray examination. A generally rectangular pedestal or base 10 has therein an interior elevator 12 which supports a non-tilting table frame 20. Frame 20 supports, for pivotal movement within the frame, a tilting table top 30 which carries a rotatable cradle or basket 50 in which the patient is placed and strapped for X-ray examination. Supported at one end of the non-tilting table frame 20 is an angulation or tilt mechanism 40 by means of which the pivotal table top 30 is moved angularly between the horizontal position illustrated in FIG. 1 and an inclined position such as is illustrated in FIG. 2 in which the head end 131 of the table top 30 is elevated, and the foot end 31 is lowered. The angulation mechanism 40 is designed to provide a maximum angle of inclination of the order of 30° from the horizontal, thereby to provide for perpendicular X-ray visualization in the oblique half-axial position of the left anterior descending coronary artery and its branches.

The base or pedestal 10 is of known construction, and so is interior elevator 12. Elevator 12 may preferably contain a motor driven raising and lowering jack screw drive, and an under-table X-ray tube and collimator which is raised when the non-tilting table frame 20 is raised, thereby to maintain constant patient focal distance in relationship to the image receptor located above the table top.

The non-tilting table frame 20, in addition to being raised and lowered by the interior elevator 12, is movable transversely and also longitudinally on the elevator 12. Transverse movement is provided by four sets of paired rollers 15. Two of the paired sets of rollers 15 are mounted on a cross bar 14 fixed to the top of elevator 12 at the left edge, and the other two sets are mounted on a cross bar 16 fixed to the right edge of the elevator top. Each set comprises an upper roller and a lower roller, as best seen in FIG. 4 which shows the forward and rearward sets of rollers on the left cross bar 14. Also mounted on the cross bars 14 and 16, are guide rollers such as rollers 17 seen in FIG. 4.

For transverse movement, table top 20 is mounted on a pair of cross channel members 24 and 26, one of which 24 is seen in FIG. 4. The horizontal lower legs of the channel members 24, 26 are received between the upper and lower rollers of the pairs 15. Thus, channel members 24,26, and the structure which is supported on channel members 24,26, are movable as a unit back and forth on the pedestal 12.

The non-tilting table frame 20 is also movable in its lengthwise direction. The means which provide for lengthwise movement are best seen in FIG. 4. Supported on each of the members 24,26 is a cross member 25 to the opposite ends of which are mounted pairs of rollers. There are four sets of such paired rollers, two sets of forward rollers 126 and two sets of rearward rollers 26. One set of each is visible in FIG. 4. Rollers 26,126 are carried transversely when the non-tiltable table frame 20, including cross frame members 24,25, is moved transversely on rollers 15. Rollers 26,126 do not move lengthwise. These rollers 26,126 support the table frame 20 for movement in its lengthwise direction.

At each side of the non-tiltable table frame 20 is a lengthwise extending beam or tube of hollow square cross section, identified 21 on the one side and 121 on the other. Secured, as by welding, to the underside of each of the square tubes 21 and 121 is an elongated member 22, 122, of C-cross section. The lower leg of each of the C-members 22 and 122 is received between the paired rollers 26, 126 and is supported on the lower of the rollers. By the means just described, the table frame 20, comprising on the one side the beam members 21 and 22 and on the other side the beam members 121 and 122, is movable in its lengthwise direction on the four sets of paired rollers 26 and 126. The lengthwise-extending beam members 21,22 and 121,122 are connected on the left end by cross member 23 and at the right end by a cross tube 27. Cross tube 27 contains a drive shaft 71 which is a part of the tilt mechanism 40, as will be described.

According to the present invention, a table top 30 carrying a patient rotator basket 50 is mounted for pivotal inclination or angulation within the frame 20. The means provided for achieving angulation are designed to tilt the table top 30 and its rotatable basket 50 in a safe and controlled manner so that the patient may be examined in any position between the horizontal and a position which is inclined at an angle of approximately 30° relative to the horizontal.

The angulation drive mechanism is at the foot end of table frame 20, and includes the side plates 41 and 141, one on each side of frame 20. As best seen in FIG. 4, the side plates 41 and 141 are mounted on and secured, as by welding, to the lengthwise-extending tubular beams 21 and 121. Side plates 41 and 141 are of generally hook-shaped configuration each having a depending leg portion through which runs an arcuate slot identified 42 and 142, respectively. Positioned at each end of slots 42 and 142, on each side of the frame 20, are sprockets, the upper sprockets being identified 80 and 180 and the lower sprockets being identified 82 and 182. Trained over the upper and lower sprockets, on each side of the table frame 20, is an endless chain, identified 81 and 181. Each of the chains 81 and 181 is tensioned by a third sprocket, identified 83 and 183. Chains 81 and 181 are guided along the outer edges of the slots 42 and 142 by angle members 43 and 143.

The manner in which the table top 30 is mounted for pivotal tilting within the non-tilting frame 20 will now be described. The pivot means at each side of the frame 20 are similar, and thus the means at but one side, the rear side, will be described.

Inserted transversely into lengthwise-extending square tube 21, at a mid-point thereof, are a pair of bushings 27,29 for receiving the outward end of a pivot pin or stud 23 which is inserted from the inward side through a lengthwise extending lower beam member 35 of table top 30. Plates 28 and 38 secure the bushings 27 and 29. Plates 36 and 37 support the pivot pin 21.

Table top 30 includes, at each side, the elongated lengthwise-extending beam 35, 135 referred to above. These beams are tubular, being of hollow square cross section. Supported on the top of tubular beams 35 and 135, at each side of the frame, are elongated hollow square tubes 34 and 134 through which pass connecting drive shafts (not shown) which extend from one end of the table to the other and connect the drive mechanisms in end housings 31 and 131 which drive the patient-receiving basket 50 rotationally and laterally. Such drive mechanisms are shown and described in my U.S. Pat. No. 3,757,129, granted Sept. 4, 1973.

Supported across one end of table top 30, on or at one end of lengthwise-extending end beams 34 and 134, is housing 131, and supported across the other end of table top 30 on or at the other end of beams 34 and 134 is another end housing 31. Projecting axially inwardly from each of the end housings 131 and 31 is a short shaft or trunnion, 132 and 32, respectively, and supported for rotation on trunnions 132 and 32 is the rotatable cradle or basket 50 having ends 151 and 51 which support therebetween an arcuate or dished panel 53 on which the patient is supported. Contained within the housings 131 and 31 are carriage means in which the trunnions are journalled and drive mechanisms for driving the trunnions 132 and 32 rotationally, thereby to rotate the cradle or basket 50 about its axis to any desired position, together with drive means for moving the carriage laterally thereby to move the cradle or basket 50 laterally. Since such drive means are disclosed in my U.S. Pat. No. 3,757,129, it is unnecessary to describe the same further in the present application. In the present application, housing 131 is at the head end and housing 31 is at the foot end. As will be seen from FIG. 2, the head end is elevatable; the foot end is not.

In the description of FIGS. 1 and 2, reference was previously made to side plates 41, 141, to slots 42, 142, and to endless chains 81, 181. Reference is now made to FIGS. 5 and 6 for further details of endless chains 81, 181 and the way in which the chains are employed to tilt the table top 30 in a controlled manner within the horizontally-fixed frame 20. FIG. 5 is a view looking at the right end side of the frame 20 and table top 30, while FIG. 6 is a view in section, looking down along the line 6—6 in FIG. 5.

Secured to chains 81 and 181 on each side of the table top is a connector bracket such as connector bracket 44 seen in FIGS. 5 and 6. As seen in FIG. 6, passing through the leg of connector bracket 44 is a screw stud 46 having a threaded end which is screwed into the side of housing 31 at the foot end of table top 30. Supported on stud 46 is a slot-follower roller 45 having a reduced diameter portion 47 which is received within and travels along slot 42 seen in FIG. 5.

Chain connector and slot-follower roller means similar to that shown in FIGS. 5 and 6 and just described are also provided on the other side of the table top. It will therefore be seen that simultaneous movement of endless chains 81 and 181 on their respective sprockets 80, 82 and 180, 182, will cause the connector brackets such as 44 and the slot follower rollers such as 45, 47 to move along their respective slots 42, 142, thereby to carry the housing 31 to a position below the horizontally-fixed table frame 20, thereby to tilt the table top 30 to the desired angle of inclination within the range of the tilt apparatus 40. In the embodiment shown and described, it is assumed that an inclined position having a maximum angle of the order of 30° relative to the horizontal, will be satisfactory for the cardiology X-ray examination for which the table top is designed.

The means for providing the power or force for driving the endless chains 81,181 need be provided at but one side of the table-top end. In the embodiment now being described, such power means are provided at the right hand side, as viewed looking from right to left in FIGS. 1–3. While the power means could be motorized, it is safer, and therefore preferable, that the power be manual, and accordingly manual drive means are illustrated and described, as best seen in FIGS. 5–8.

As seen in FIGS. 5–8, a hand crank 61 is provided at one end of a shaft 62. Mounted on crank shaft 62, and preferably integral therewith, is a worm 63 which is in mesh with a worm gear 64 mounted on a shaft 65 supported in a gear reducing housing 60. Also mounted on and secured to shaft 65 is a spur gear 66 which is in mesh with and drives a pinion 67 mounted on and secured to a shaft 68 supported in housing 60. Also supported on and secured to shaft 68 is a spur gear 69 which is in mesh with and drives a pinion 70 which is mounted on and secured to a sprocket shaft 71. Sprocket shaft 71 is contained within cross tube 27 and extends the full width of the table top from one side to the other. Shaft 71 is journalled at the one side in housing 60 and side plate 41 and at the other side in side plate 141.

Mounted on and secured to shaft 71 at one side of the table top is sprocket 80 and at the opposite side sprocket 180, and trained over the sprocket 80 and 180 are endless chains 81 and 181, respectively.

It will be seen that by rotating the hand crank 61, chains 81 and 181 may be moved thereby moving connector brackets 44,144, thereby moving the slot-follower rollers 45,145, thereby moving the housing 31. Without being limited to the values about to be mentioned, it may be said that tilting table tops in accordance with the present invention have been constructed having a gear-reducing mechanism of the type shown and just described with gear ratios chosen to effect an overall speed reduction of 4:1, thereby to reduce what would have been a 100-pound load on a direct-drive hand crank to a 7-pound load.

Means are also provided for locking the tiltable table top 30 in the horizontal position. While such locking means may take different forms, one suitable form is illustrated in FIG. 9. As there shown, mounted in side plate 41 is a lock-pin housing 90 having a screw cap 91 having a central hole through which passes lock 92 pin having at its inward end an enlarged head 93. Lock pin 92 is spring loaded outwardly by spring 94 which bears against head 93. Screwed onto the outer end of lock pin 92 is a knurled pull knob 98.

As seen in FIG. 5, secured to side panel of foot-end table-top housing 31 is a plate 95 having an inclined surface 96 which serves as a cam to depress lock pin 92 when the table top 30 is returned from inclined to horizontal position. Located in plate 95 below the inclined surface 96 is a hole 97 adapted to receive lock pin 92. A similar locking mechanism is provided on each side of the foot end of table top 30.

Assuming that table top 30 is locked in horizontal position, as illustrated in FIG. 9, and that it is desired to raise the head end 131 of the table top to a position such as 30° above horizontal for cardiology examination, the operator first withdraws lock pin 92 by pulling out pull knob 98 against the action of biasing spring 94. The operator then turns crank 61 to lower the foot end 31 of table top 30 until the desired angular position is reached.

When the foot end 31 of table top 30 is returned from its lowered position to horizontal position, the projecting lock pin 92 is engaged by the inclined surface 96 of plate 95 and is cammed inwardly against the action of spring 94. When lock pin 92 comes into registry with hole 97, the pin enters the hole to lock the table top in horizontal position.

When table top 30 has been placed in a particular angular position by the crank operator, it is maintained in that angular position by the locking action of worm 63 on worm gear 64.

It will be understood that before the operator operates the crank 61 to lower the foot end of the table top to a particular angular position, he moves the table frame 20 horizontally from a central position such as is shown in FIG. 1 to an off-center position such as is shown in FIG. 2 so that the foot end of the table top 30, when lowered, will clear the pedestal 12 and base 10.

It will be seen that from the foregoing description that, by the present invention, an X-ray examination table is provided which is particularly useful for cardiology X-ray examination work in which the examining physician is able to get very close to the elevated head of the patient. Prior art X-ray examination tables which have tilting facilities are much too bulky for close examination work.

The tiltable X-ray examination table provided in accordance with the present invention has the capability of placing the patient in a wide variety of desired positions. The patient, strapped in the cradle or basket 50, is fully rotatable about the lengthwise axis of the basket to any desired angular position. The basket 50 is also movable laterally or transversely relative to the tilting table top. See my U.S. Pat. No. 3,757,129. The tilting table top, supported on the non-tiltable table frame 20, is movable in both the lengthwise and lateral directions. It is also elevatable by the elevator 12. A motor drive unit in the base elevator 12 provides an undertable X-ray tube and fluoroscopic collimator mount for use with over-table image amplifiers. When used in conjunction with the cradle tilt mechanism of the present invention, the motor drive automatically raises and lowers the X-ray tube as the cradle is tilted and brought back to horizontal to assist in reducing the patient focal spot distance change.

Heavy duty all-steel welded construction is used for maximum table top cantilevered strength, rigidity and reliable continued serviceability. Bearing carriage mounts are provided between the table base elevator 12 and the table frame 20 or cradle table top 30.

While, as has been described, the tilting mechanism for the table top 30 provides for up to 30 percent angulation of the cradle top, with the head end in the "up" position, in actual practice, 20 percent is normally a sufficient angulation to provide for convenient perpendicular visualization in the oblique half-axial position of the left anterior descending coronary artery and its branches with minimal patient longitudinal centering adjustment being necessary during angulation. The patient angulation is accomplished safely and quickly by the manual operation of crank handle 61 located at the foot end 31 of the table frame 20 where the technician or operator is conveniently out of the way of the examining physician and primary radiation.

What is claimed is:

1. Apparatus for supporting a patient for X-ray examination, said apparatus comprising:
   a. a pedestal base;
   b. an elongated non-tilting table frame;
   c. support means supporting said table frame horizontally on said base and adapted for moving said frame in the transverse and lengthwise direction relative to said base;

d. an elongated tilting table top;

e. pivotal means mounting said table top on said frame for tilting movement about its transverse axis;

f. a cradle for receiving a patient for X-ray examination;

g. support means supporting said cradle on said table top for rotational movement about the longitudinal axis of said cradle; and h. a tilting mechanism comprising;

h-1 a pair of side plates, one plate mounted on each side of said non-tilting table frame at one end thereof, each of said plates provided with a fixed guide slot for guiding said table top during tilting movement, h-2 sprocket and endless-chain drive means mounted on each of said plates for moving said tilting table top along said guide slots, and h-3 a cross-shaft carries and interconnects drive sprockets mounted in each side plate.

2. Apparatus according to claim 1 wherein the drive means of said tilting mechanism includes;

a. a drive worm mounted in one of said side plates;

b. a worm gear in mesh with and driven by said drive worm;

c. gear reducer means interposed between said worm gear and said cross-shaft carrying a drive sprocket.

3. Apparatus according to claim 2 wherein;

a. lock means are provided for locking said table top relative to said table frame.

4. Apparatus according to claim 3 wherein:

a. said pedestal base includes an interior elevator;

b. said non-tilting table frame is mounted on said elevator.

* * * * *